US00PP37633P2

(12) United States Plant Patent
Hansoti

(10) Patent No.: US PP37,633 P2
(45) Date of Patent: Aug. 18, 2026

(54) ***SANSEVIERIA* PLANT NAMED 'HANSOTI64'**

(50) Latin Name: *Sansevieria trifasciata*
Varietal Denomination: HANSOTI64

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 19/349,669

(22) Filed: Oct. 3, 2025

(51) Int. Cl.
*A01H 6/12* (2018.01)
*A01H 5/12* (2018.01)

(52) U.S. Cl.
USPC ..... Plt./382

(58) Field of Classification Search
USPC ..... Plt./382
CPC ..... A01H 6/12; A01H 5/12
See application file for complete search history.

*Primary Examiner* — Keith O. Robinson

(57) ABSTRACT

A new and distinct cultivar of *Sansevieria* plant named 'HANSOTI64' is disclosed, characterized by foliage having a silvery-green upper surface with prominent transverse banding of dark green and a central wide band with creamy streaks of 1 D. Foliage characteristically lacks a variegated margin, making the bright interior color more prominent. Plants of the "Bird's Nest" type of *Sansevieria*, generally small and suitable for pots around 12 cm. Plants are usefully very long lasting under low light indoor conditions. The new variety is a *Sansevieria*, typically produced as an ornamental plant.

12 Drawing Sheets

Latin name of the genus and species: *Sansevieria trifasciata.*

Cultivar denomination: 'HANSOTI64'.

BACKGROUND OF THE INVENTION

The present invention relates to a new and distinct cultivar of *Sansevieria* plant, botanically known as *Sansevieria trifasciata* of the family Asparagaceae, hereinafter referred to by the cultivar name 'HANSOTI64'. *Sansevieria* has now been reclassified as *Dracaena* meaning this new cultivar could also be correctly referred to as *Dracaena trifasciata.*

*Sansevieria* is a monocotyledonous plant with fleshy, succulent leaves which are available in a huge range of species, varieties and cultivars as an outdoor ornamental plant (under tropical or warm temperate conditions) or as indoor plants. Both, the parental 'Hansoti40' U.S. Plant Pat. No. 36,221 and the new cultivar 'Hansoti64' belong to the group of *Sansevieria trifasciata* called "Birds Nest" or 'Hahnii' *Sansevieria* Group of very short or dwarf cultivars all ultimately derived from the original *Sansevieria trifasciata* 'Hahnii' patented in 1941 (U.S. Plant Pat. No. 470), in contrast to the medium sized "Compact *Sansevieria* Group" with *Sansevieria trifasciata* 'Futura Superba', unpatented as the typical example, and the "Tall *Sansevieria* Group" of *Sansevieria trifasciata* cultivars with tall leaves up to or even beyond 4 feet (1.25 meters) tall and *Sansevieria trifasciata* 'Laurentii', unpatented as the typical example.

The new *Sansevieria* 'HANSOTI64' was discovered and selected by Mr. Ashish Hansoti, as a single aberrant side shoot within a planting of *Sansevieria trifasciata* 'Hansoti40', a patented 'Hahnii' or "Birds Nest" type of *Sansevieria* selected and grown at this nursery at Village Asle, District Satara, Maharashtra State in Western India. Thus, it originated as a naturally occurring mutation from *Sansevieria trifasciata* cultivar 'Hansoti40' (U.S. Plant Pat. No. 36,377) in April of 2022.

Asexual reproduction of the new *Sansevieria* cultivar 'Hansoti64' by vegetative cuttings was first performed around March of 2023 and continued propagation and selection of true to type material was continued at Village Asle, District Satara, in Maharashtra State in Western India. After several rounds of selection of true to type shoots and discarding of off-types, it was seen that the distinctive combination of characteristics of the new cultivar reproduced true to type as long as the propagation was done through side shoots originating from the base of the parent plant (basal suckers). Thus, it can be said that the new cultivar reproduces true to type through side shoots (basal suckers) only.

BRIEF SUMMARY OF THE INVENTION

The following traits have been repeatedly observed and are determined to be unique characteristics of 'HANSOTI64', which in combination distinguish this *Sansevieria* as a new and distinct cultivar:

1. Vivid and distinct, broad central band of longitudinal light golden yellow/greenish yellow streaks along length of the leaf lamina.
2. This is combined with the transverse banding typical of most *Sansevieria trifasciata* cultivars but in this case this banding is more prominent and vivid because the area between the darker cross hatching is cream rather than silvery-green. Both combine to give the whole rosette a bright look seen in only a few other cultivars of the 'Hahnii' type.
3. Another way to describe the rosette of 'Hansoti64' is to say it's like *S. trifasciata* 'Green Compacta', unpatented but with the additional central band of bright yellowish green and a more vivid crossbanding giving an overall extra-bright appearance to the whole rosette.

Leaf width is quite variable and the strongest, healthiest plants have the widest leaves; this is true across all *Sanse-*

*vieria trifasciata* cultivars known to the inventor. This variation means leaf width can be anything from 6 cm to 8 cm wide depending on season, growing conditions and plant vigour and plant age. The leaves are lanceolate with a firm, waxy texture. The blades are thick & fleshy.

The new cultivar is moderately drought tolerant and adapts well to conditions of bright light and heavy shade (exterior and interior). The intensity of these central bands varies with exposure to light and the contrast is most intense under higher light conditions. The plant is liable to get scorched in full hot tropical sun.

The leaves are an overall dark green color, on closer examination consisting of silvery green background color with typical darker green trifasciata cross-hatching along with a unique and distinct longitudinal band consisting of lighter creamy green streaks, which is the new and unusual feature of 'Hansoti64'.

The silvery-green background areas of the leaves are close to 191A and the dark green cross-hatching shows coloration similar to N189A. The central band of creamy streaks and bands is near 1D. Going across this creamy band are the typical cross hatching of *S. trifasciata* but here, lacking the silvery-green background, the green cross-hatching shows as a bright green close to 143A while the lighter areas are close to 1D. It is to be noted that this creamy band is brightest in young and recently mature leaves and slowly becomes more and more greenish till, in older leaves, this creamy area is changed almost entirely to the silvery-green seen in the leaf outer areas, with the central "light" band barely discernible.

The backside of the leaves has a somewhat different coloration to the front, in young and recently mature leaves the overall background color is a silvery-grey with a creamy overlay, looking like 191C and the cross-hatching bands are a little narrower. The central broad longitudinal band is quite muted but is still seen on the back of the leaves. As the leaves age this central band practically disappears and leaves look like any typical *S. trifasciata* cultivar such as 'Green Compacta'.

PARENTAL COMPARISON

Plants of the new *Sansevieria* 'HANSOTI64' are similar to plants of the parental cultivar, however, 'HANSOTI64' differs in the characteristics described in Table I.

TABLE I

Comparison of Parental and the New cultivar 'Hansoti64'

| | Characteristic | Parent Cultivar 'Hansoti40' U.S. Plant Pat. No. 36,377 | New cultivar 'Hansoti64' |
|---|---|---|---|
| 1. | Leaf size | 12 to 14 cm long, 6-7 cm wide | 12 to 13 cm long, 6-8 cm wide |
| 2. | Number of leaves | 9 to 11 leaves | 11 to 13 leaves |
| 3. | Variegation Pattern | Cream border on dark green leaves with typical *S. trifasciata* transverse banding plus a wide central band of light green/creamy yellow streaks | Creamy border is entirely missing; a prominent central band of creamy color dominates the leaves, especially the young and recently mature leaves. |
| 4. | Border variegation | 1 to 12 mm wide cream border | None, no border variegation |

TABLE I-continued

Comparison of Parental and the New cultivar 'Hansoti64'

| | Characteristic | Parent Cultivar 'Hansoti40' U.S. Plant Pat. No. 36,377 | New cultivar 'Hansoti64' |
|---|---|---|---|
| 5. | Central Variegation | 20 to 30 mm wide band of lighter green/creamy yellow streaks on top of and in addition to the transverse banding. | 20 to 30 mm wide band of lighter green/creamy yellow streaks on top of and in addition to the transverse banding. |

COMMERCIAL COMPARATOR

'Hansoti64' is similar to the old, familiar green *S. trifasciata* 'Hahnii' U.S. Plant Pat. No. 470 with the addition of a prominent creamy band in the centre of the leaf and brighter cross-banding and lacking the border bands. The lack of this border band, in some ways, enhances the contrast and impact of the central bright band of creamy yellow lines and streaks.

Plants of the new *Sansevieria* 'HANSOTI64' are similar to the commercial cultivar *Sansevieria* 'Green Compacta', unpatented. 'Green Compacta' is a superior, compact growing form of 'Hahnii' selected and grown by the inventor. Plants of the new *Sansevieria* 'HANSOTI64' differ from plants of the commercial cultivar in the characteristics described in Table II.

TABLE II

Comparison of similar cultivar 'Green Compacta' and the new cultivar 'Hansoti64'

| | Characteristic | Similar Cultivar 'Green Compacta' | New cultivar 'Hansoti64' |
|---|---|---|---|
| 1. | Leaf size | 9 to 13 cm long | 12 to 13 cm long, 6-8 cm wide |
| 2. | Number of leaves | 9 to 12 leaves | 11 to 13 leaves (somewhat more leaves) |
| 3. | Variegation Pattern | Bright central band along length of leaf. Transverse banding essentially not seen. | Creamy border is entirely missing; a prominent central band of creamy color dominates the leaves, especially the young and recently mature leaves. |
| 4. | Border variegation | 2 to 12 mm wide creamy band with inconspicuous transverse banding. | None, no border variegation |
| 5. | Central Variegation | Only the central bands of creamy streaks seen on dark green background with no transverse banding in leaf central area. | 20 to 30 mm wide band of lighter green/creamy yellow streaks on top of and in addition to the extra-prominent transverse banding. |

BRIEF DESCRIPTION OF THE PHOTOGRAPHS

The accompanying photographs illustrate the overall appearance of the new *Sansevieria* cultivar 'HANSOTI64' showing the colors as true as is reasonably possible with colored reproductions of this type. Colors in the photographs may differ slightly from the color value cited in the detailed botanical description which accurately describe the color of 'HANSOTI64'.

These pictures illustrate the plant form which is the unique characteristic of 'HANSOTI64' and at the same time demonstrates comparisons with both the parent cultivar and the comparator 'Hansoti26'. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 1:
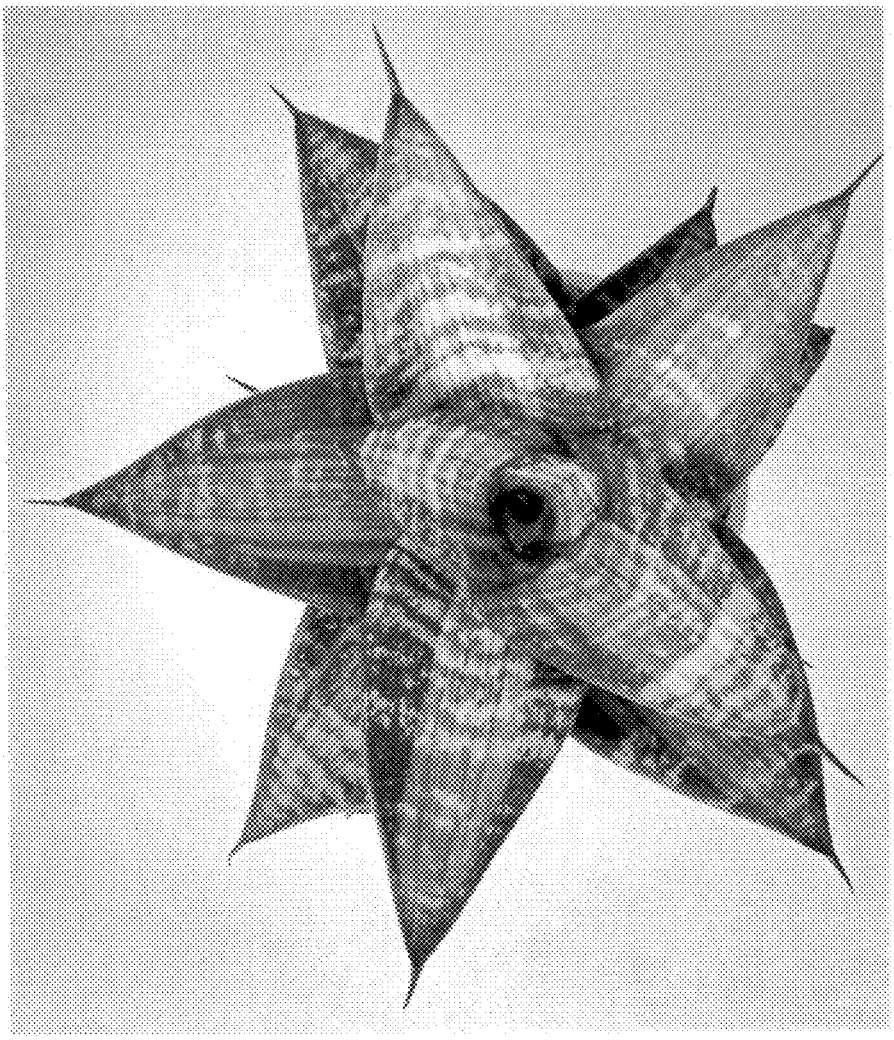
FIG. 1 illustrates a top-down view of *Sansevieria* 'HANSOTI64' in a 12 cm pot. This plant is 3 months old from a rooted cutting.
Figure 2:
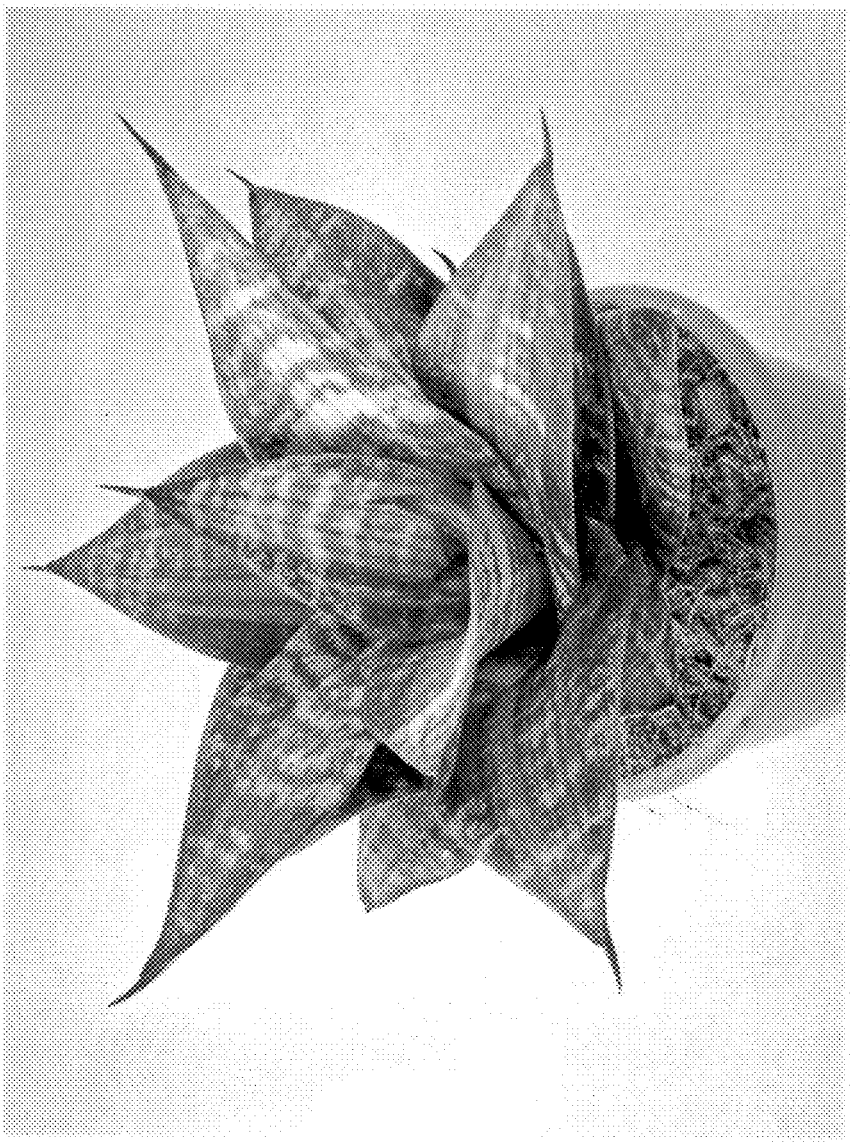
FIG. 2 illustrates the same plant as FIG. 1 from above at a 45-degree angle.
Figure 3:
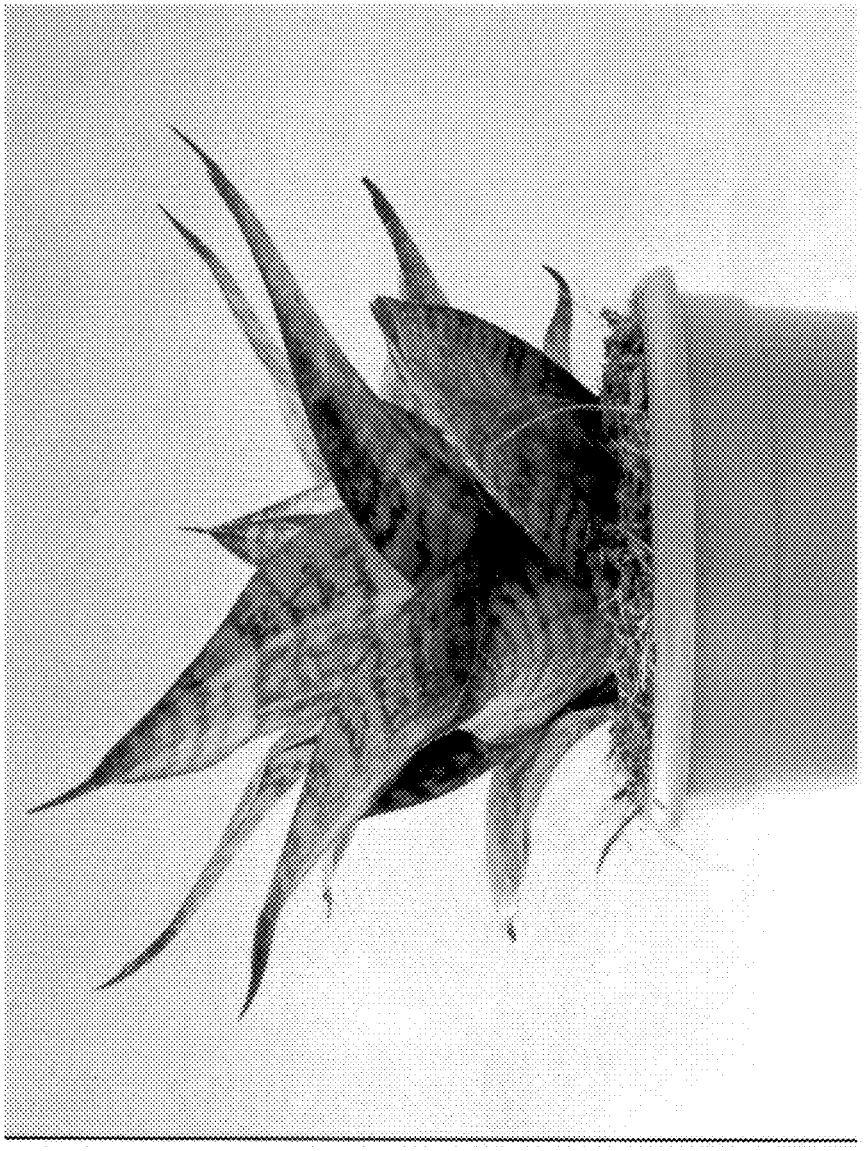
FIG. 3 illustrates the same plant as FIG. 1 from a side view.
Figure 4:
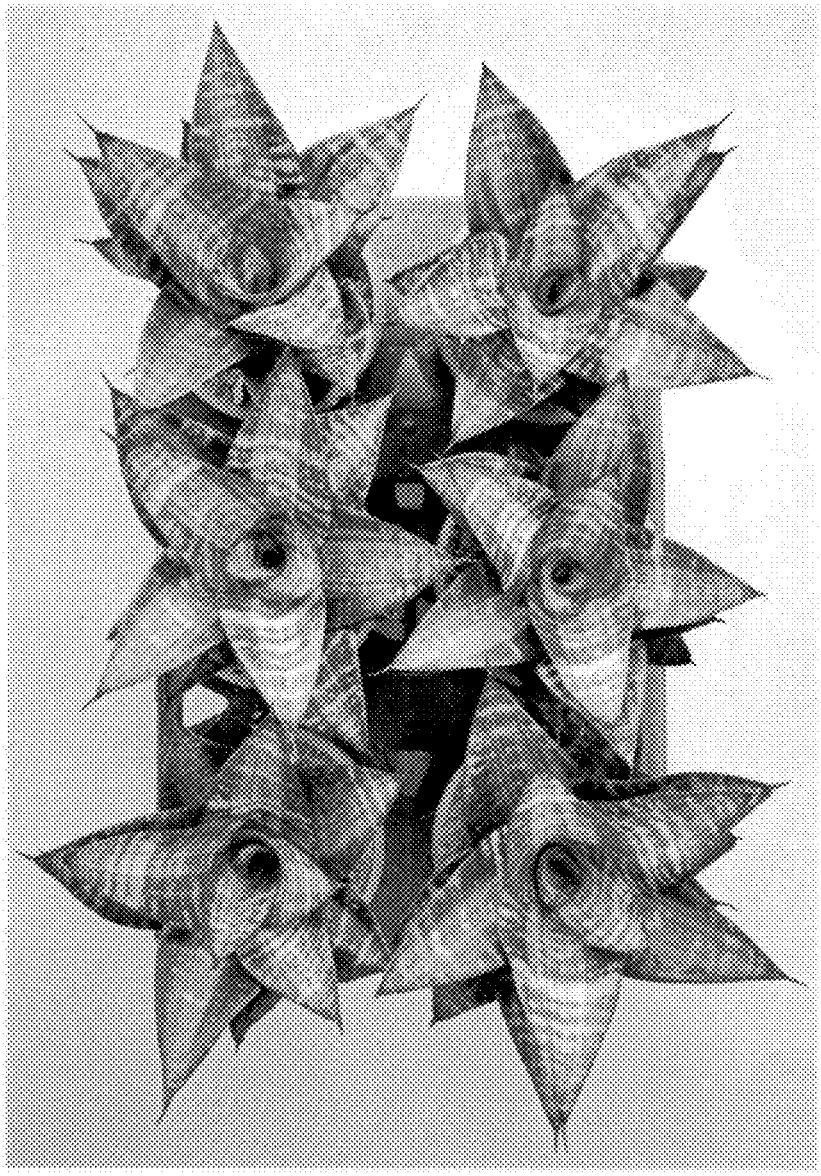

FIG. 4 shows a group of 6 'Hansoti64' plants in a tray, showing uniformity across multiple plants of this new cultivar. Plants are in 12 cm pots and approximately 3 months old. The photograph was taken from a top-down view.

Figure 5:
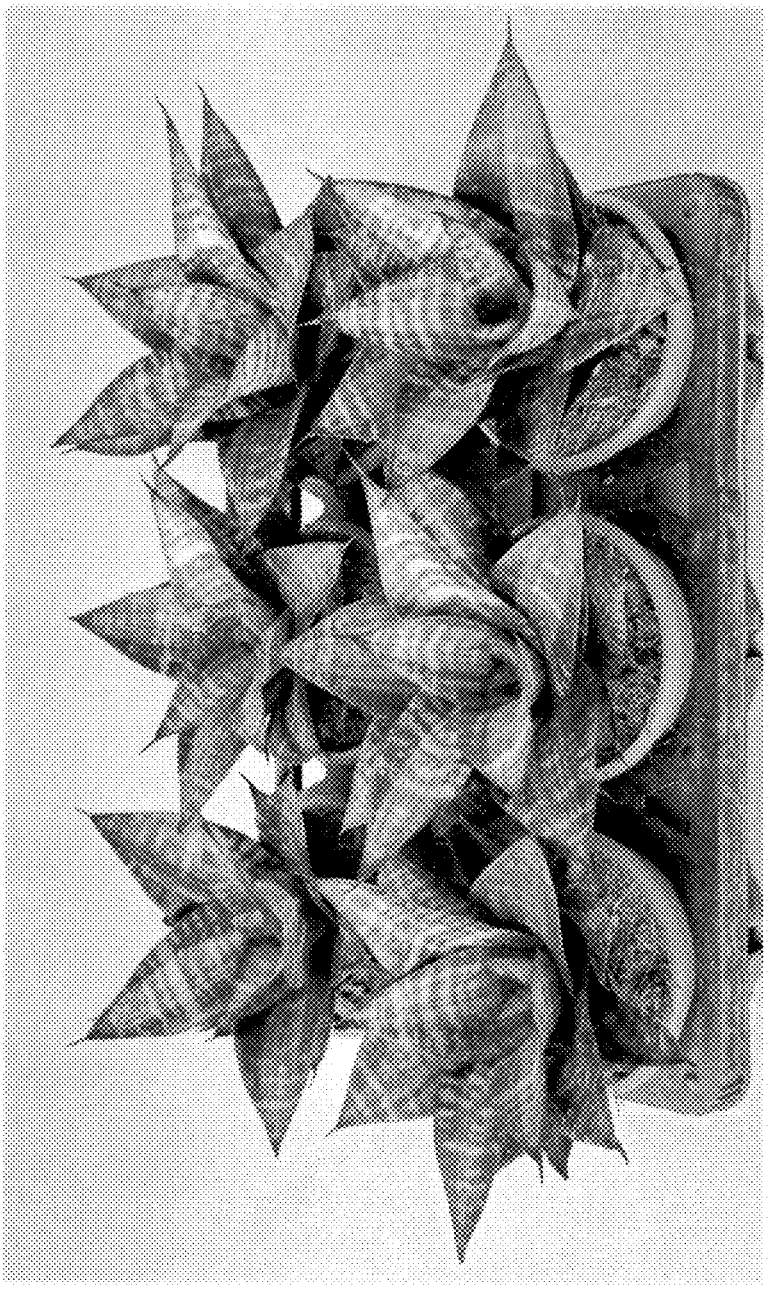

FIG. 5 is a photograph of the same plants as in FIG. 4. This photograph was taken from above at a 45-degree angle.

Figure 6:
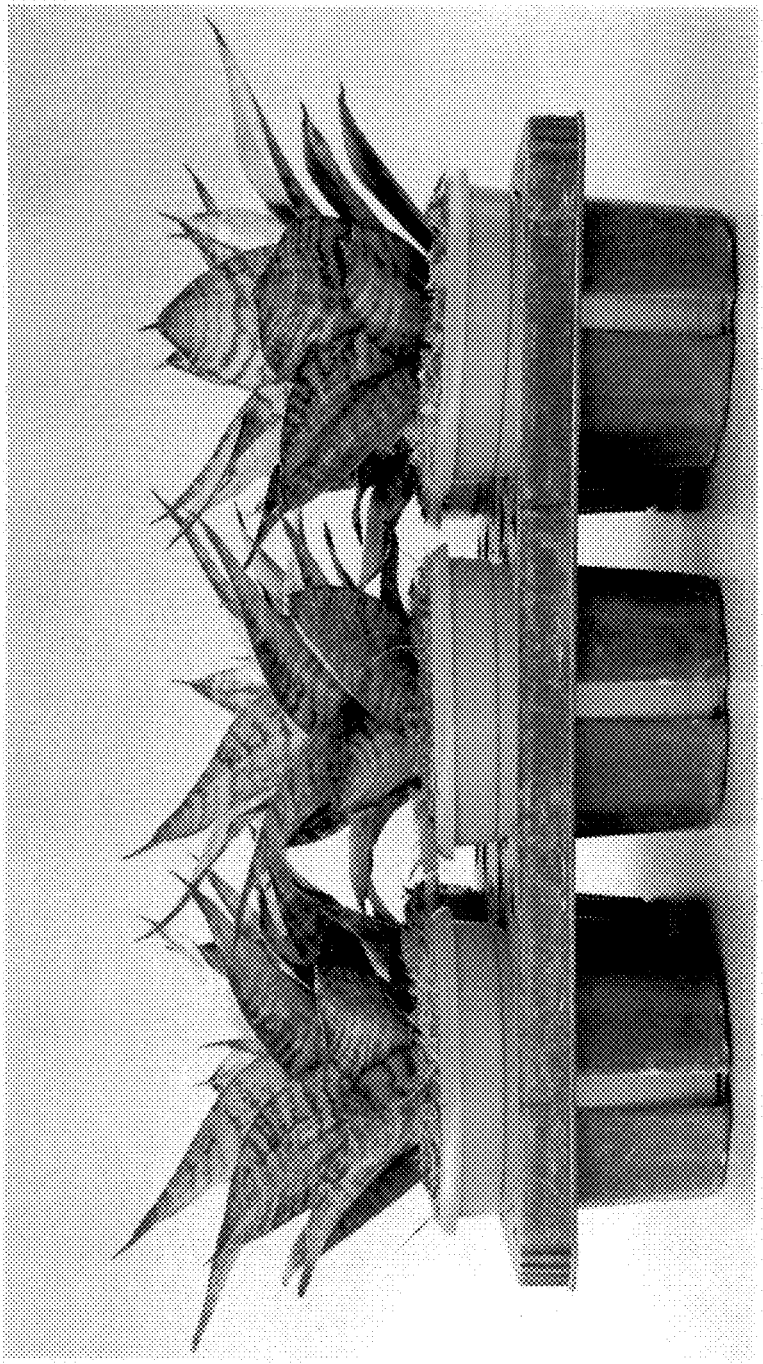

FIG. 6 is a photograph of the same plants as in FIG. 4. This photograph was taken from a side view, showing the underside of the leaves.

Figure 7:
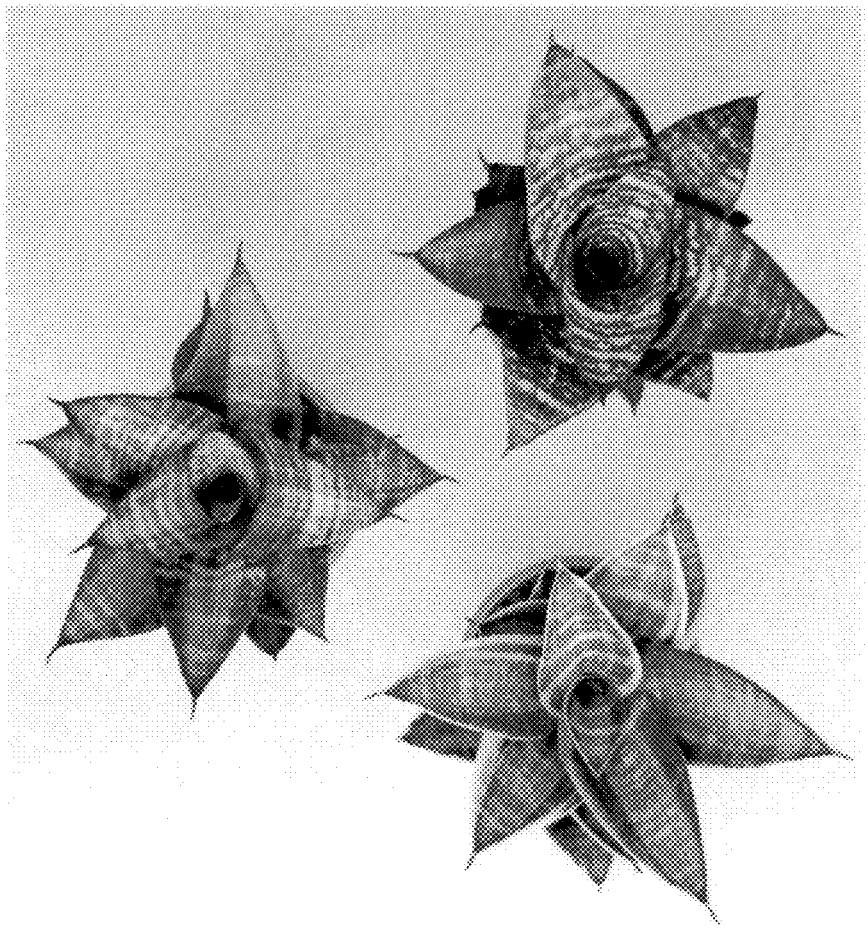

FIG. 7 is a comparison of plants of 'HANSOTI64' (upper, center) with plants of the parent cultivar, 'Hansoti40' (bottom left) and comparator 'Green Compacta' (bottom right). All plants are 12 weeks old from a rooted cutting. This photograph was taken from a top-down view.

Figure 8:
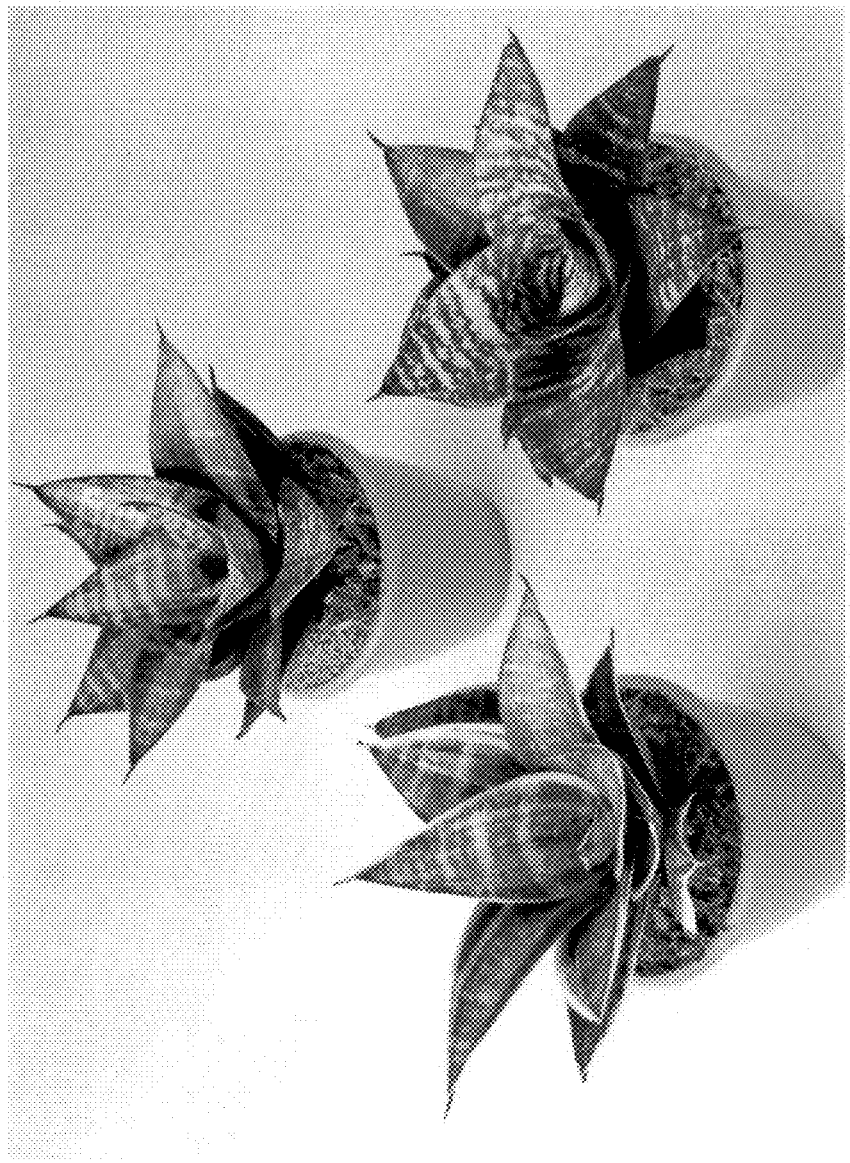

FIG. 8: is a photograph of the same plants as in FIG. 7, taken from above at a 45-degree angle. 'HANSOTI64' (center), the parent cultivar, 'HANSOTI40' (left) and comparator 'Green Compacta' (right). All plants are 3 months old from a rooted cutting. This photograph was taken from a top-down view.

Figure 9:
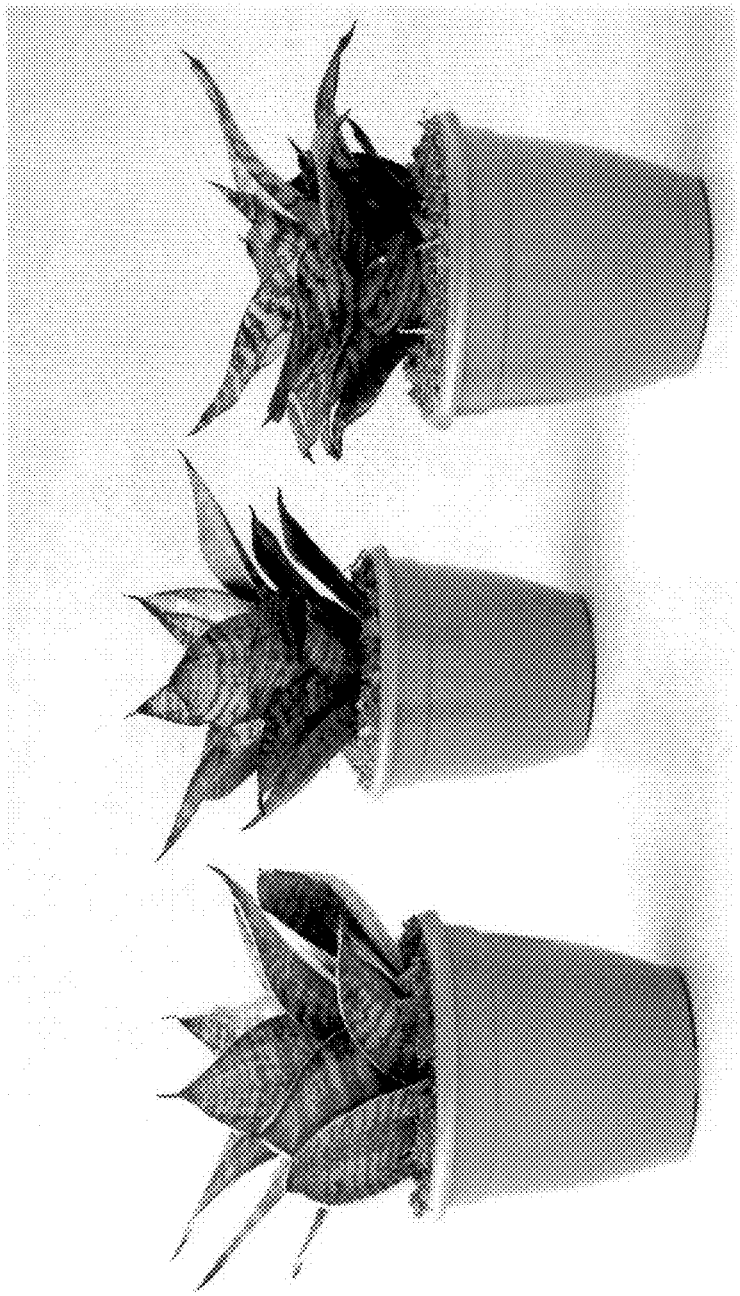
Figure 10:
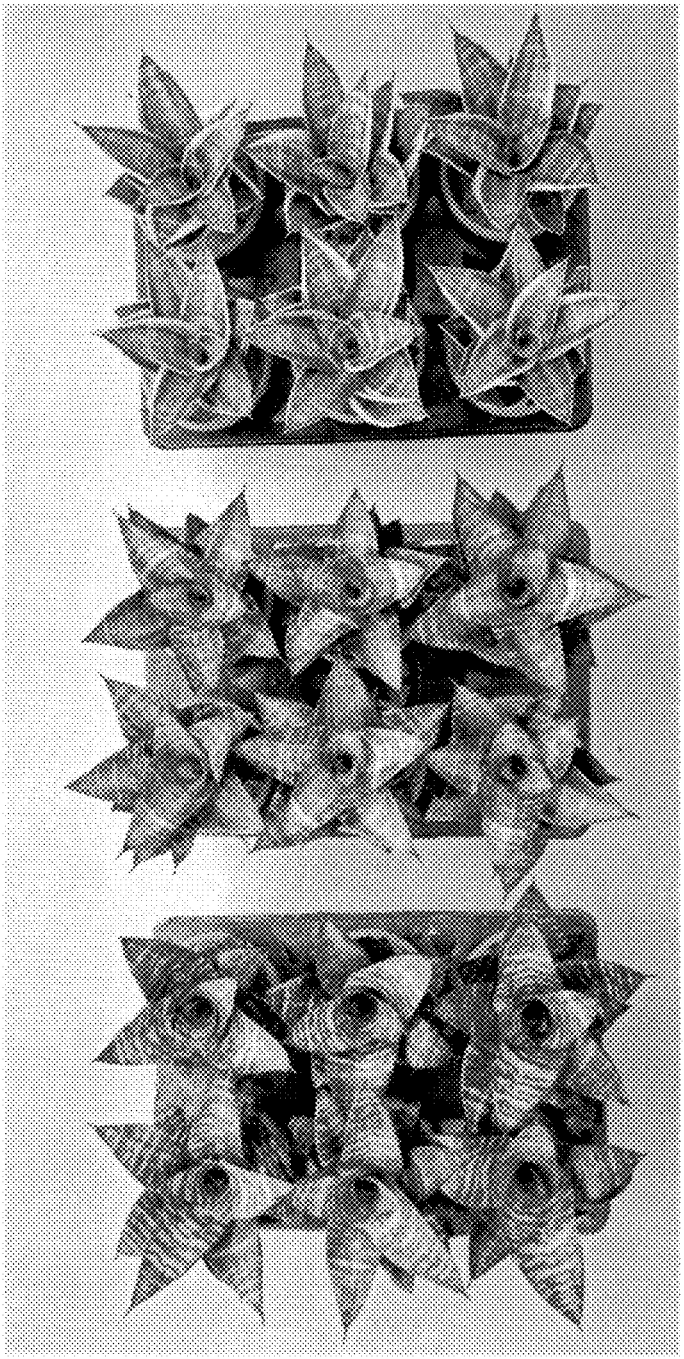

FIG. 9 is a photograph of the same plants as in FIG. 7 and FIG. 8, taken from a side-view. 'HANSOTI64' (center), the parent cultivar, 'HANSOTI40' (left) and comparator 'Green Compacta' (right). All plants are 3 months old from a rooted cutting. This photograph was taken from a side-view FIG. 10 is a comparison of trays holding 6 plants each of 'HANSOTI64' (center) with the parent cultivar, 'HANSOTI40' (right) and comparator 'Green Compacta' (left). All plants are 3 months old from a rooted cutting. This photograph was taken from a top down view.

Figure 11:
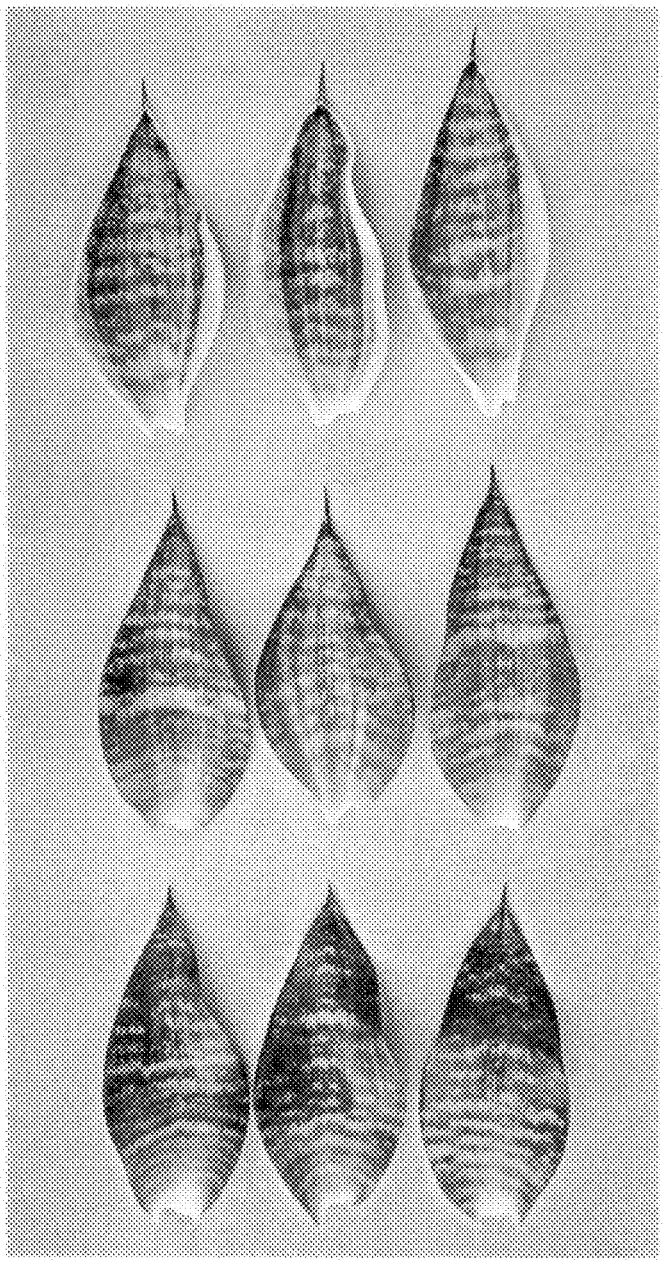

FIG. 11 is a comparison of adaxial leaf surfaces of the parental cultivar 'Hansoti40' (top), comparator 'Green Compacta' (bottom) and 'Hansoti64' (center).

Figure 12:
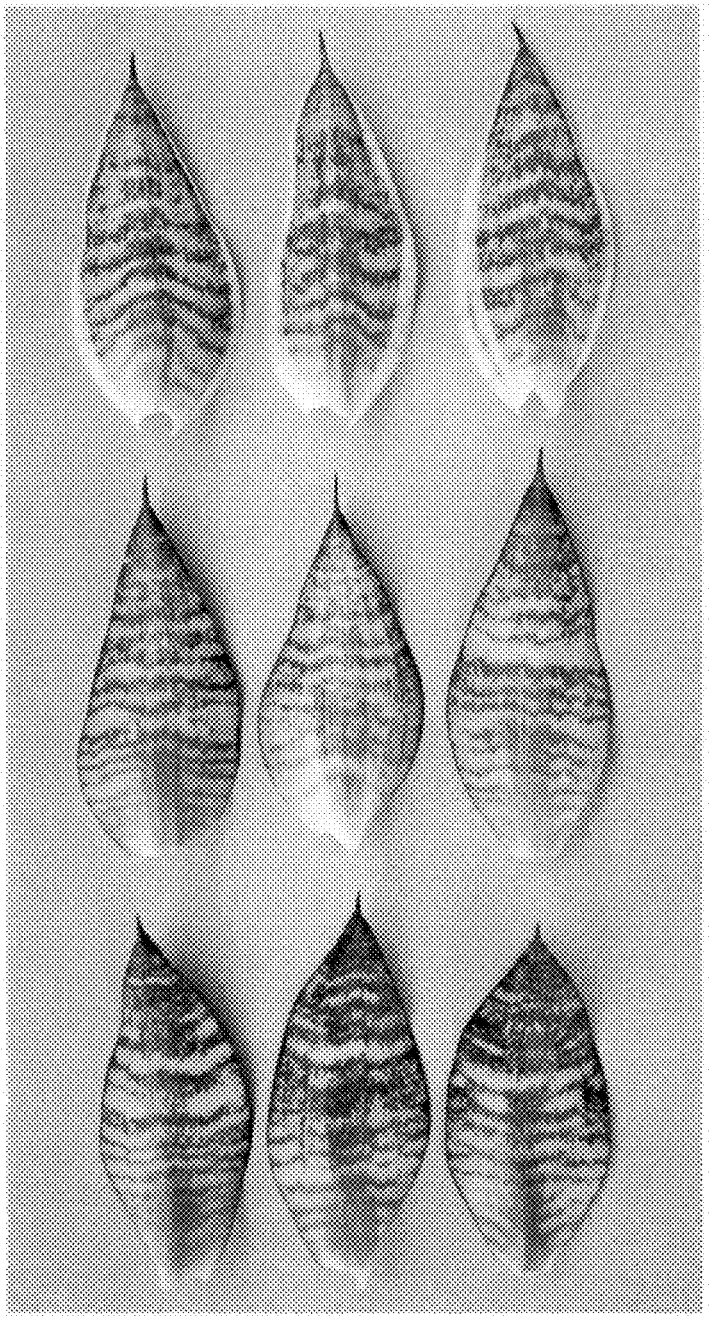

FIG. 12 is a comparison of abaxial leaf surfaces of the parental cultivar 'Hansoti40' (top), comparator 'Green Compacta' (bottom) and 'Hansoti64' (center).

DETAILED BOTANICAL DESCRIPTION

The new *Sansevieria* 'HANSOTI64' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI64' plants grown in an open poly house (high tunnel) at Village Asle, District Satara, Maharashtra State in Western India. Average temperature in Asle is 25° C., with summer highs of 39° C. and winter lows of 6° C. Plants grow under natural light conditions and between 30% to 75% shade levels depending on the season (higher shade in hot summer conditions).

This crop gets nearly constant fertilization to increase production. Controlled release fertilizer 13:11:11 Type 360-days release at 1 kilo/cubic meter of media, liquid fertilizer at approximately 100 ppm N, 20 ppm P and 100 ppm K, along with complete micronutrients. Production is closely related with proper and complete plant nutrition and an open soilless growing media based on coconut coir. The plants are grown in plastic pots on metal benching in spacing trays.

Color references are made to The Royal Horticultural Society Colour Chart (R.H.S.), 2007 ($5^{th}$ Edition), except where general colors of ordinary significance are used. It should be noted that colors in *Sansevieria* are somewhat variable depending on light levels, nutrition balance, age of plant and other factors. Plant & leaf size, width, thickness and color can vary considerably depending on light levels, feed composition and EC and pot size.

The photographs and descriptions were taken during the winter season in Asle, District Satara, Maharashtra State, India when outdoor day and temperatures were 32° C. to 38° C. and nights, usually of 25° C. to 28° C. The age of the plants described is 3-4 months in 12 cm pots.

Botanical classification: *Sansevieria trifasciata* 'HANSOTI64'.

General information:

*Parentage*.—Single aberrant side shoot within a planting of *Sansevieria trifasciata* 'Hansoti40' U.S. Plant Pat. No. 36,377.

*Optimal growth conditions*.—High adaptability to outdoor or indoor conditions.

*Light intensities*.—High adaptability to outdoor or indoor conditions but needs some shade in hot climates.

*Temperature*.—Day: 25° C. to 35° C. Night: 15° C. to 25° C.

*Temperature tolerance*.—Tolerant to a low temperature of about 6° C. and a high temperature of 38° C. and above, very heat tolerant.

*Fertilization*.—Constant feed of 100 ppm N, 20 ppm P and 100 ppm K is used along with micronutrients with occasional leaching. Media incorporation of 13:11:11 Type 360 days release at 1 kg/cubic meter of media.

*Growth regulators*.—Not necessary for growing this cultivar. Rooting hormone helps rapid and prolific rooting of offsets.

Propagation:

*Typical*.—Vegetative, by side suckers which come true to type. Does not come true from leaf cuttings.

*Rooting habit and description*.—Rhizomes elongated, fleshy, giving rise to offsets (side shoots). Offsets root easily with fibrous adventitious roots from cut end.

*Time to initiate roots*.—25 to 30 days at 25° C. to 30° C.

*Time to produce a rooted liner*.—About 45 days at 25° C. to 30° C.

*Time to produce ready* 12 *cm potted plant from liner*.—About 10 to 12 weeks at 25° C. to 30° C.

Plant:

*General appearance and form*.—Monocot; leaf bases arranged in a rosette around growth point.

*Height*.—About 8 to 10 cm when grown in 12 cm pots.

*Diameter*.—About 16 to 18 cm when grown when grown in a 12 cm size container.

*Rosette height* (*center*).—About 4 to 6 cm.

*Rosette diameter*.—About 16 to 18 cm.

*Shape*.—Inverted triangle.

*Fragrance*.—None.

*Stem*.—Modified rhizome which are fleshy with erect foliage. Texture: Smooth, waxy. Color: Yellow Green 144C. Strength: Strong and durable.

*Internode length*.—About 1 mm.

Foliage:

*Quantity*.—About 11 to 13 in ready to sell plant in a 12 cm pot. Number slowly increases with age.

*Arrangement and attachment*.—Single, alternate; leaf bases arranged stiffly in a rosette around growth point.

*Leaf length*.—About 12 to 13 cm in mature, full-size leaf.

*Leaf width*.—About 6 to 8 cm in mature, full-size leaf.

*Overall shape of leaf*.—Lanceolate.

*Apex shape*.—Acute, triangular and aristate with soft tip.

*Base shape*.—Truncate.

*Margin*.—Entire. Sharp.

*Texture*.—Upper Surface: Smooth and waxy texture.

*Texture*.—Under Surface: Smooth and waxy texture.

*Pubescence*.—None.

*Attachment*.—Sessile.

Color recent mature leaf:

Upper surface: Basal silvery-green color near 191A with prominent transverse banding of dark green close to N189A and central wide band with creamy streaks of 1D.

*Margin variegation*.—None.

Crossbanding: Typical crossbanding as seen in most *S. trifasciata* cultivars with dark green color near N189A. Along the central creamy band the crossbanding is a bright green near 143A (there being no silvery-green underlay due to the creamy streaks) while the areas between these bands is a creamy yellow near 1D, giving a brightly striped appearance.

Lower surface: Still prominent transverse banding but with narrower dark bands as above and the longitudinal creamy band is less prominent, and this characteristic of the top surface is much subdued but still perceptible on the bottom surface. The silvery-grey areas between the darker banding are overlaid with a light creamy layer so that this area is now neared 191C.

*Venation pattern*.—Longitudinal/parallel to leaf shape. No color distinct from leaf blade.

*Leaf fragrance*.—None.

Other:

*Inflorescence description*.—Flowers not observed to date.

*Weather resistance*.—Moderately drought tolerant.

*Pest resistance*.—Reasonably resistant to pests, susceptible to root mealybugs (*Rhizoecus pritchardi*). Typical pests include *Pseudococcidae longispinus* and *Tetranychus urticae*.

*Disease resistance*.—Occasionally shows *Anthracnose*. Largely disease-free from clean mother stock and appropriate disease mitigation measures undertaken.

*Fruit/seed production*.—No fruits/seeds detected to date.

What is claimed is:

1. A new and distinct cultivar of *Sansevieria* plant named 'HANSOTI64' as herein illustrated and described.

* * * * *